(12) United States Patent
Parniak et al.

(10) Patent No.: US 7,439,035 B1
(45) Date of Patent: Oct. 21, 2008

(54) METHOD OF IDENTIFYING OR CHARACTERIZING A COMPOUND THAT MODULATES RIBONUCLEASE H ACTIVITY

(75) Inventors: Michael A. Parniak, Pittsburgh, PA (US); Kyung-Lyum Min, Montreal (CA)

(73) Assignee: McGill University, Montreal, Quebec (CA)

( * ) Notice: Subject to any disclaimer, the term of this patent is extended or adjusted under 35 U.S.C. 154(b) by 0 days.

(21) Appl. No.: 11/656,977

(22) Filed: Jan. 24, 2007

Related U.S. Application Data (62) Division of application No. 10/238,952, filed on Sep. 11, 2002, now Pat. No. 7,186,520.

(60) Provisional application No. 60/318,359, filed on Sep. 12, 2001.

(51) Int. Cl.
*C12Q 1/37* (2006.01)

(52) U.S. Cl. .............................. 435/23; 435/6; 435/199; 436/24.3

(58) Field of Classification Search .................... 435/23, 435/6, 199; 436/24.3
See application file for complete search history.

(56) References Cited

U.S. PATENT DOCUMENTS

| | | | |
|---|---|---|---|
| 6,268,146 B1 * | 7/2001 | Shultz et al. | 435/6 |
| 6,287,765 B1 * | 9/2001 | Cubicciotti | 435/6 |
| 6,573,045 B1 * | 6/2003 | Karn et al. | 435/6 |
| 6,773,885 B1 * | 8/2004 | Walder et al. | 435/6 |

* cited by examiner

*Primary Examiner*—Ralph Gitomer (57) ABSTRACT

The invention relates to a substrate and method for the assay of ribonuclease H activity. The substrate comprises a DNA/RNA heteroduplex molecule having fluorophore and quencher molecules in close proximity, which emit a background level of fluorescence in the absence of ribonuclease H activity due to quenching of the fluorophore as a result of fluorescence resonance energy transfer. Ribonuclease H cleavage of the heteroduplex results in an increase in fluorescence emission due to the destabilization and separation of the DNA and RNA molecules and their associated fluorophore and quencher molecules. The assay method of the present invention is suitable for use in screening (e.g. high throughput screening) for modulators, e.g. inhibitors, of the ribonuclease H activity associated with, for example, reverse transcriptase and ribonuclease H enzymes.

12 Claims, 3 Drawing Sheets

```
5'- GAU CUG AGC CUG GGA GCU - fluorescein - 3'  SEQ ID NO: 1
3'- CTA GAC TCG GAC CCT CGA - DABCYL     - 5'  SEQ ID NO: 2

OR

5'-fluorescein- GAU CUG AGC CUG GGA GCU - 3'  SEQ ID NO: 3
3'-DABCYL-      CTA GAC TCG GAC CCT CGA - 5'  SEQ ID NO: 4

OR

5'-fluorescein- GAU CUG AGC CUG GGA GCU - fluorescein - 3'  SEQ ID NO: 5
3'-DABCYL-      CTA GAC TCG GAC CCT CGA - DABCYL      - 5'  SEQ ID NO: 6
``` where fluorescein is

R = 5'-aminolink RNA and where DABCYL is

R = 3'-aminolink-DNA

```
                          SEQUENCE LISTING

<160> NUMBER OF SEQ ID NOS: 8

<210> SEQ ID NO 1
<211> LENGTH: 18
<212> TYPE: RNA
<213> ORGANISM: Artificial Sequence
<220> FEATURE:
<223> OTHER INFORMATION: Modified RNA oligonucleotide
<220> FEATURE:
<221> NAME/KEY: modified_base
<222> LOCATION: (8)..(8)
<223> OTHER INFORMATION: 3'-uracil modified by a fluorescein group

<400> SEQUENCE: 1
gaucugagcc ugggagcu                                                  18

<210> SEQ ID NO 2
<211> LENGTH: 18
<212> TYPE: DNA
<213> ORGANISM: Artificial Sequence
<220> FEATURE:
<223> OTHER INFORMATION: Modified DNA oligonucleotide
```

```
<220> FEATURE:
<221> NAME/KEY: modified_base
<222> LOCATION: (1)..(1)
<223> OTHER INFORMATION: 5'-adenine modifed with a DABCYL group

<400> SEQUENCE: 2
agctcccagg ctcagatc                                                 18

<210> SEQ ID NO 3
<211> LENGTH: 18
<212> TYPE: RNA
<213> ORGANISM: Artificial Sequence
<220> FEATURE:
<223> OTHER INFORMATION: Modified RNA oligonucleotide
<220> FEATURE:
<221> NAME/KEY: modified_base
<222> LOCATION: (1)..(1)
<223> OTHER INFORMATION: 5'-guanine modified by a fluorescein group

<400> SEQUENCE: 3
gaucugagcc ugggagcu                                                 18

<210> SEQ ID NO 4
<211> LENGTH: 18
<212> TYPE: DNA
<213> ORGANISM: Artificial Sequence
<220> FEATURE:
<223> OTHER INFORMATION: Modified DNA oligonucleotide
<220> FEATURE:
<221> NAME/KEY: modified_base
<222> LOCATION: (18)..(18)
<223> OTHER INFORMATION: 3'-cytosine modified by a DABCYL group

<400> SEQUENCE: 4
agctcccagg ctcagatc                                                 18

<210> SEQ ID NO 5
<211> LENGTH: 18
<212> TYPE: RNA
<213> ORGANISM: Artificial Sequence
<220> FEATURE:
<223> OTHER INFORMATION: Modified RNA oligonucleotide
<220> FEATURE:
<221> NAME/KEY: modified_base
<222> LOCATION: (1)..(1)
<223> OTHER INFORMATION: 5'-guanine modified by a fluorescein group
<220> FEATURE:
<221> NAME/KEY: modified_base
<222> LOCATION: (18)..(18)
<223> OTHER INFORMATION: 3'-uracil modified by a fluorescein group

<400> SEQUENCE: 5
gaucugagcc ugggagcu                                                 18

<210> SEQ ID NO 6
<211> LENGTH: 18
<212> TYPE: DNA
<213> ORGANISM: Artificial Sequence
<220> FEATURE:
<223> OTHER INFORMATION: Modified DNA oligonucleotide
<220> FEATURE:
<221> NAME/KEY: modified_base
<222> LOCATION: (1)..(1)
<223> OTHER INFORMATION: 5'-adenine modified by a DABCYL group
<220> FEATURE:
<221> NAME/KEY: modified_base
<222> LOCATION: (18)..(18)
<223> OTHER INFORMATION: 3'-cytosine modified by a DABCYL group
```

```
-continued

<400> SEQUENCE: 6
agctcccagg ctcagatc                                                         18

<210> SEQ ID NO 7
<211> LENGTH: 18
<212> TYPE: RNA
<213> ORGANISM: Artificial Sequence
<220> FEATURE:
<223> OTHER INFORMATION: 5'-[32P]-RNA

<400> SEQUENCE: 7
gaucugagcc ugggagcu                                                         18

<210> SEQ ID NO 8
<211> LENGTH: 18
<212> TYPE: DNA
<213> ORGANISM: Artificial Sequence
<220> FEATURE:
<223> OTHER INFORMATION: Complementary unlabeled DNA

<400> SEQUENCE: 8
agctcccagg ctcagatc                                                         18
```

METHOD OF IDENTIFYING OR CHARACTERIZING A COMPOUND THAT MODULATES RIBONUCLEASE H ACTIVITY

REFERENCE TO RELATED APPLICATIONS

This application is a division of application Ser. No. 10/238,952 filed Sep. 11, 2002, now U.S. Pat. No. 7,186,520, which claims the benefit of U.S. Provisional Application No. 60/318,359, filed Sep. 11, 2001, the content of both of which is herein incorporated by reference.

FIELD OF THE INVENTION

The invention relates to a substrate and method for the assay of ribonuclease H activity and uses thereof.

BACKGROUND OF THE INVENTION

Ribonuclease H(RNase H) is one of a family of enzymes termed nucleases, which act to hydrolyse nucleic acids. RNase H is unique among nucleases in that it selectively degrades the RNA component of an RNA/DNA duplex molecule, a double-strand nucleic acid comprised of one strand of ribonucleic acid (RNA) bound to a complementary strand of deoxyribonucleic acid (DNA) via Watson-Crick base pairing. Ribonuclease H enzymes are ubiquitous, found in virtually all organisms, as well in several types of virus[1].

Ribonuclease H performs critical functions in the replication of several human pathogenic viruses, including retroviruses such as the human immunodeficiency virus (HIV) types 1 and 2, and the human T-cell leukaemia viruses (HTLV) types 1 and 2. In addition, ribonuclease H is essential for the replication of the human hepadnavirus, hepatitis B virus (HBV).

Retroviral Ribonuclease H. Retroviruses carry their genetic information as RNA, but must replicate through a double-strand DNA intermediate. Thus, following recognition and entry into a susceptible cell, the retroviral genomic RNA must be converted into viral DNA. Multiple steps are involved in this crucial step of replication, each of which is catalyzed by the retroviral enzyme reverse transcriptase (RT). This enzyme is therefore multifunctional, and possesses three enzymatic activities, RNA-dependent DNA polymerase activity (RDDP), DNA-dependent DNA polymerase activity (DDDP), and ribonuclease H activity (RNase H).

Several retroviruses are human pathogens. These include the human immunodeficiency viruses type 1 and 2 (HIV-1 and HIV-2), and the human T-cell leukemia viruses types 1 and 2 (HTLV-1 and HTLV-2). Of these, HIV-1 is by far the most serious pathogen. HIV-1 infection leads to AIDS, an incurable and inevitably fatal disease. Since identification of the virus in the early 1980's, it is estimated that more than 58 million individuals have been infected with HIV-1, and of these nearly 25 million have died of AIDS. HIV-1 infection remains one of the most serious infectious disease problems worldwide.

A variety of biological agents are currently in use for the treatment of HIV-1 infections. HIV-1 RT has been, and remains, an important target for antiviral development. Many inhibitors of HIV-1 RT have been discovered, including nucleoside reverse transcriptase inhibitors (NRTI) such as 3'-azido-3'-deoxythymidine (AZT) and 2',3'-dideoxy-3'-thiacytidine (3TC) and nonnucleoside reverse transcriptase inhibitors (NNRTI) such as nevirapine, delavirdine and efavirenz (for a recent review see reference 2). However, virtually all inhibitors of HIV-1 RT are directed against the RDDP and/or DDDP activity of RT. Very few inhibitors of the ribonuclease H activity of HIV-1 (and HIV-2) reverse transcriptase have been described, and none are in clinical use.

Although current therapeutics are initially very effective at controlling the course of HIV spread in an infected individual, thereby improving the quality of life and longevity of HIV-infected patients, prolonged therapy inevitably leads to viral resistance to these drugs. Resistance to RT inhibitors correlates with mutations in RT, and resistance to protease inhibitors correlates with mutations in the HIV protease. Clinical appearance of drug-resistant HIV imparts an unfavorable prognosis. In addition, the transmission of drug-resistant HIV variants from an infected treated individual to a previously naïve individual is becoming a serious problem. Drug therapies for use by these newly infected patients are restricted because of the infection by drug-resistant virus. There is therefore an urgent need to identify new inhibitors of HIV replication, especially inhibitors that act on new viral targets, not presently targeted by current chemotherapies. These new targets include the ribonuclease H activity associated with the viral reverse transcriptase. Current assays for this enzyme activity are cumbersome and time-consuming, and unsuitable for high-throughput screening of the large chemical libraries available to major pharmaceutical companies. In order to identify inhibitors of this viral enzyme, more appropriate assays are needed, particularly assays suitable for high-throughput screening of large libraries of chemical compounds.

Hepadnaviral Ribonuclease H. Human hepatitis B virus (HBV) is a major worldwide health threat and is responsible for the majority of the 1 to 2 million deaths annually from hepatitis. HBV is a member of the hepadnavirus family. Hepadnaviruses are small enveloped DNA viruses that replicate through an RNA intermediate. This replication mechanism therefore requires reverse transcription, to convert the RNA intermediate into viral DNA, a process carried out by the hepadnaviral P protein. As is the case with retroviral reverse transcriptases, hepadnaviral P protein must be multifunctional to carry out reverse transcription. Thus, the protein possesses RNA-directed DNA polymerase and DNA-directed DNA polymerase activities, and ribonuclease H-activity.

There are very few treatments available for HBV infection. These include interferon therapy or liver transplantation, both of which are expensive and at best only partially successful. Recently, the nucleoside analog 3TC has been approved for treatment of chronic infection and transplant patients. This nucleoside is directed against the DNA polymerase activity of the HBV DNA polymerase (hepadnaviral P protein). Additional therapies need to be developed. The hepadnaviral P protein-associated ribonuclease H provides a target for this development. Again, as is the case for retroviral RT RNase H, assays for this enzyme activity are cumbersome and time-consuming, and unsuitable for high-throughput screening of the large chemical libraries available in major pharmaceutical companies. In order to identify inhibitors of this viral enzyme, improved assays are needed, e.g. suitable for high-throughput screening of large libraries of chemical compounds.

Assays for Ribonuclease H Activity. Several types of assays for ribonuclease H have been described. For the large part, these assays involve the use of radiolabeled RNA/DNA duplex substrates. RNase H degradation of the radiolabeled RNA strand releases small RNA fragments which are then measured and/or visualized by various means, including liquid scintillation counting, autoradiography, etc.

1. Radioactivity release assay[3,4]. In this assay, the RNA/DNA hybrid duplex substrate is prepared such that the RNA is uniformly radiolabeled throughout its length either by incorporation of [$^3$H]-NTPs or [$\alpha$-$^{32}$P]-NTPs during in vitro synthesis of the RNA transcript used in the preparation of the RNA/DNA duplex substrate. Incubation of the radiolabeled RNA/DNA hybrid duplex substrate with RNase H results in degradation of the RNA into small radiolabeled RNA fragments (generally less than or equal to 3 nucleotides in size). The reaction is stopped and any unreacted large radiolabeled RNA/DNA hybrid duplex substrate is then precipitated by the addition of acid. After high-speed centrifugation, aliquots of the supernatant are counted by liquid scintillation spectrometry. The amount of radioactivity in the supernatant is directly related to the extent of RNase H degradation of the radiolabeled RNA/DNA hybrid duplex substrate. In a variation of this method[4], the synthetic radiolabeled RNA/DNA hybrid duplex substrate is immobilized on nitrocellulose filters by UV irradiation. Treatment of the filters with RNase H degrades the RNA, releasing small radiolabeled fragments into the solution. RNase H activity is then measured by determining the increase in solution radioactivity, and/or by the decrease in filter-bound radioactivity, using liquid scintillation spectrometry.

2. Renaturation gel assay[5-7]. Ribonuclease H enzymes, especially those of prokaryotic origin, are readily renatured following denaturation with agents such as sodium dodecyl sulfate (SDS). In the renaturation gel assay, the RNase H is electrophoresed in an acrylamide gel in which an RNA/DNA hybrid duplex (with the RNA strand radiolabeled, usually by $^{32}$P) has been embedded by copolymerization. Following electrophoresis, the RNase H is renatured by soaking the gel in various buffers appropriate for renaturation, and then placed in a buffer that allows initiation of RNase H activity (usually by the presence of divalent metal cations such as $Mg^{2+}$ or $Mn^{2+}$). After an appropriate period (generally 15-20 hours or longer), the gel is fixed in an acidic solution, dried, and the distribution of radioactivity visualized by autoradiography. Areas of RNase H activity will appear as a light-to-white band on a dark background. This "negative" detection is difficult to quantitate accurately, thus the gel renaturation method provides only qualitative assessment of RNase H activity. A non-radioactive version of this assay has been described in which the RNA is synthesized with the fluorescent nucleotide BODIPY-TR-14-UTP. Following electrophoresis, renaturation and RNase H activity, the loss of fluorescence in the area of Rnase H is visualized by a fluorescence scanner. As with the radioactive version, this fluorescence assay is qualitative only.

3. Gel electrophoretic assay[8,9]. In this assay, the RNA is radiolabeled with $^{32}$P, either by synthesis using [$\alpha$-$^{32}$P]-NTPs, or more commonly by labeling of the 5'-end of a synthetic RNA using [$\gamma$-$^{32}$P]-ATP and bacteriophage T4 polynucleotide kinase. The [$^{32}$P]-labeled RNA is hybridized to a complementary DNA to form the RNA/DNA hybrid duplex substrate. Addition of RNase H degrades the RNA strand. The extent of degradation, and in many cases the degradation products, are visualized by removing aliquots of the reaction mixture at various times, separating the reaction products by electrophoresis on denaturing sequencing gels, followed by autoradiography. The extent of RNase H activity can be determined quantitatively by densitometric analysis of the time-dependent disappearance of the full-length RNA substrate and/or the appearance of the smaller degradation products. Variations of the gel electrophoretic assay include the use of capillary gel electrophoresis coupled with UV detection to identify degradation products[10], or visualization of unlabeled RNA degradation products after polyacrylamide gel electrophoresis using a general nucleic acid stain such as Stains-All. The latter method suffers from lack of sensitivity, especially for small RNA degradation products.

4. Other assay methods. A non-radioactive solution-phase assay has been described[11] that uses a 5'-biotin-RNA strand duplexed with a 5'-digoxigenin-DNA strand. Treatment with RNase H cleaves the biotinylated RNA from the RNA/DNA hybrid duplex substrate. Aliquots are removed at various times of reaction, and any remaining uncleaved substrate is captured onto streptavidin-coated 96-well microtiter plates followed by detection with an alkaline phosphatase-labeled anti-digoxin antibody.

All of these methods provide only discontinuous measurements of RNase H activity, and involve sample handling at fixed time points. Kinetic measurements therefore require that aliquots be removed from a reaction pool, and analyzed individually, a time-consuming process which can limit the precision of the assay. In addition, many of the methods require one or more additional steps, such as electrophoretic resolution of the degraded RNA followed by autoradiography, ELISA detection of residual unreacted modified RNA, etc. All of these additional steps add to the time needed to complete the assay. Many of these additional steps, such as electrophoretic separation of reaction products, are not amenable to high-throughput analysis.

Nucleases, which are enzymes which hydrolyze/cleave nucleic acids, are differentiated by the identity of the substrates on which they act. A variety of assays are available to measure different types of nuclease activity, including gel electrophoresis (similar to that described above), thin-layer chromatography[12], capture and elution of products from ion-exchange filters[3], etc. As with the other methods described above, none of these assays described to date are suitable for real-time kinetic measurements, and all involve one or more additional steps following the nuclease cleavage of the substrate nucleic acids.

There therefore is a need for an improved RNase H assay.

SUMMARY OF THE INVENTION

The present invention relates to a substrate and a method for assaying RNase H activity.

Accordingly, in a first aspect, the invention provides a substrate suitable for assaying ribonuclease H activity; said substrate comprising:
(a) an RNA oligonucleotide;
(b) a DNA oligonucleotide hybridized to said RNA oligonucleotide to form a heteroduplex molecule;
(c) a fluorophore attached to one of said RNA or DNA oligonucleotides; and
(d) a quencher molecule attached to the other of said RNA or DNA oligonucleotides;

wherein said fluorophore and said quencher molecule are located within close proximity of each other in said heteroduplex molecule such that fluorescence emission of said fluorophore in said heteroduplex molecule is reduced as compared to a corresponding fluorescence emission in a corresponding heteroduplex molecule lacking said quencher molecule.

In an embodiment, the fluorophore is attached to an end of one of said RNA or DNA oligonucleotides. In a further embodiment, quencher molecule is attached to an end of the other of said RNA or DNA oligonucleotides. In an embodiment, the quencher molecule is attached to an end of one of the RNA or DNA oligonucleotides and the quencher molecule is attached to an end of the other of the RNA or DNA oligonucleotides, and wherein the fluorophore and the quencher molecule are juxtaposed at an end of said heteroduplex molecule.

In an embodiment, the quencher molecule is non-fluorescent.

In embodiments, the RNA oligonucleotide and/or the DNA oligonucleotide are 14-24 nucleotides in length.

In an embodiment, the RNA oligonucleotide and the DNA oligonucleotide are exactly complementary.

In an embodiment, the fluorophore is fluorescein. In a further embodiment, the quencher molecule is DABCYL.

In another aspect, the invention provides a method for assaying ribonuclease H activity in a sample, said method comprising:
(a) measuring a first level of fluorescence emission of the fluorophore of the above-mentioned substrate in the absence of said sample;
(b) contacting the above-mentioned substrate with said sample; and
(c) measuring a second level of fluorescence emission in the presence of said sample;

wherein an increase in said second level relative to said first level is indicative of ribonuclease H activity. In embodiments said second level is at least 8 fold greater than said first level.

In an embodiment, the ribonuclease H activity is associated with a reverse transcriptase, e.g. a retroviral reverse transcriptase (e.g. from human immunodeficiency virus type 1 or 2 [HIV-1 or HIV-2]) or a hepadnavirus (e.g. human hepatitis B virus [HBV]) reverse transcriptase.

In an embodiment, the ribonuclease H activity is associated with a ribonuclease H enzyme, e.g. of a prokaryotic or eukaryotic cell (e.g. human) origin. In an embodiment, the ribonuclease H enzyme is selected from the group consisting of ribonuclease H1 and ribonuclease H2.

In another aspect, the invention provides a method of identifying or characterizing a compound capable of modulating ribonuclease H activity, said method comprising:
(a) contacting a source of enzymatically active ribonuclease H with a test compound and the above-mentioned substrate to form a reaction mixture;
(b) measuring a test level of fluorescence emission of said fluorophore; and
(c) comparing said test level of fluorescence emission with a control level of fluorescence emission obtained from a corresponding control reaction mixture lacking said test compound;

wherein a difference between said test level and said control level is indicative that said test compound is capable of modulating ribonuclease H activity. In an embodiment, the test level of fluorescence emission is less than the control level of fluorescence emission and the test compound is capable of inhibiting ribonuclease H activity.

In an embodiment, the test compound is a plurality of test compounds and the reaction mixture is a plurality of respective reaction mixtures (e.g. 2 to 96 reaction mixtures or 2 to 384 reaction mixtures).

The invention further provides commercial packages comprising the above-mentioned substrate together with instructions for (1) assaying ribonuclease H activity in a sample and/or for (2) identifying or characterizing a compound capable of modulating (e.g. inhibiting) ribonuclease H activity.

The invention further provides a use of the above-mentioned substrate for (1) assaying ribonuclease H activity in a sample or (2) identifying or characterizing a compound capable of modulating (e.g. inhibiting) RNase H activity.

BRIEF DESCRIPTION OF THE DRAWINGS

FIG. 2. Fluorescence emission spectra of the undegraded (A) and degraded (B) RNA/DNA hybrid duplex substrate. A solution of 60 μmol of the RNA/DNA hybrid duplex substrate in a total volume of 300 μl reaction buffer comprising 50 mM Tris/HCl (pH 8.0, 37° C.) and containing 60 mM KCl and 2.5 mM $MgCl_2$ was prepared and placed into a single cell fluorescence cuvette. The sample excited at 490 nm, and the fluorescence emission measured over the range of 500-600 nm, using a Quanta Master QM-1 T-format fluorescence spectrometer (Photon Technology International, Princeton, N.J.). This spectrum is indicated as A in the Figure. After the emission spectrum was obtained, an aliquot of p51/p66 HIV-1 RT heterodimer was added (to give a final concentration of 2 nM RT), and the sample was mixed and incubated at 37° C. for 30 minutes. This treated sample was then excited at 490 nm, and the fluorescence emission measured over the range of 500-600 nm. This spectrum is indicated as B in the Figure.

FIG. 3. Time- and enzyme concentration-dependence of the FRET assay of the ribonuclease H activity of HIV-1 reverse transcriptase. Aliquots of 85 μl of 50 mM Tris/HCl (pH 8.0, 37° C.), containing 60 mM KCl and 2.5 mM $MgCl_2$, and 0.2 μM of the RNA/DNA hybrid duplex substrate were added to individual wells of a fluorescence microtiter plate and warmed to 37° C. using the temperature control of the SpectraMax Gemini XS microplate spectrofluorometer. Reactions were started by the addition of 5 μl of various solutions of recombinant HIV-1 reverse transcriptase such that the final concentration of RT in the individual assays ranged from 0.1 nM to 5 nM of p51/p66 heterodimer, and mixing using the automatic mixing function of the microplate spectrofluorometer. The increase in fluorescence at 528 nm was measured at regular time intervals using excitation at 490 nm and a 515 nm cut-off filter. The time-dependent increase in fluorescence signal due to hydrolysis of the RNA component of the hybrid duplex substrate at each of the different RT concentrations is shown in panel A. Under these conditions, the rate of increase of fluorescence emission at 528 nm was found to be directly proportional to the concentration of RT in the assay, as shown in panel B.

DETAILED DESCRIPTION OF THE INVENTION

A number of continuous spectrophotometric assays, based on fluorescence, have been described to measure the cleavage of double-stranded DNA by restriction enzymes[14,15] and by HIV-1 integrase 6. These assays in general involve fluorescence resonance energy transfer (FRET), which is the transfer of electronic excitation energy from a fluorescent donor chromophore to an unexcited acceptor chromophore. If the donor and acceptor are sufficiently close in proximity, energy transfer will be facilitated, thereby reducing the fluorescence emission of the donor chromophore. Separation of the donor and acceptor chromophores will result in the appearance of donor fluorescence emission. While the methods which have been described are able to provide real-time measurements of the cleavage of the double-stranded DNA, they are not particularly sensitive due to inefficient quenching of the donor fluorescence.

Ghosh et al[14] prepared synthetic DNA with an internal PaeR7 restriction enzyme recognition site, and labeled with the fluorescent dye fluorescein at the 5'-end of one DNA strand, and with the fluorescent dye rhodamine at the 5'-end of the complementary DNA strand. The rhodamine provided a degree of quenching of the fluorescein emission at 518 nm, when samples were excited at 480 nm. Addition of the restriction enzyme PaeR7 resulted in the single-site cleavage of both strands of DNA, separating the 5'-fluorescein and 5'-rhodamine fluorophores, and leading to an increase in fluorescence emission. This method is most applicable to short DNA sequences, since the degree of fluorescein emission quenching by the rhodamine acceptor decreases with increasing length of the DNA. In addition, the use of the rhodamine fluorophore as FRET acceptor is not completely efficient, thus providing a sizable background signal[14] that can impact on the sensitivity of the assay. As well, the fluorescence emission of the 5'-fluorescein DNA fragment may not be optimal, due to internal quenching of fluorescein emission by stacking interactions with the surrounding residual double-strand DNA helix.

Lee et al[15] studied the BamHI restriction enzyme cleavage of a 14 nucleotide DNA strand labeled at the 5'-end with fluorescein, annealed to an unlabeled complementary DNA oligonucleotide. The fluorescein emission was partially quenched due to the stacking effects of the surrounding double-strand DNA helix. Treatment of this DNA with BamH1 resulted in the single-site cleavage of both strands of the DNA, resulting in a partial removal of quenching and the appearance of a fluorescent signal. As with the PaeR7 restriction enzyme assay, this method is most applicable to short DNA sequences. The method also lacks sensitivity since the quenching of the 5'-fluorescein by stacking effects of the surrounding double-strand DNA helix is only partial, thereby providing a relatively large background fluorescent signal for the uncleaved DNA substrate. Indeed, only a two-fold increase in fluorescence emission was noted in this system[15].

Lee et al[16] prepared double-stranded DNA in which one of the strands possessed an internal 5-amino(12)-2'-dUMP residue, and the other strand possessed a 5-amino(12)-2'-dUMP residue at the 5'-end of the oligonucleotide. The internal 5-amino(12)-2'-dUMP residue was modified with fluorescein, and the 5'-5-amino(12)-2'-dUMP residue on the other strand was labeled with the fluorescent dye eosin. In this construct, eosin acted as FRET acceptor. Cleavage of this substrate by HIV-1 integrase resulted in an approximately 2- to 3-fold increase in fluorescent signal over a time period of about 60 minutes[16].

The FRET assays described to date are not especially sensitive, due to incomplete quenching of the donor fluorophore's fluorescence emission, leading to unacceptable variability in signal at early times of reaction or when the extent of cleavage is low. The latter is an important factor when assessing inhibitor action, since inhibition of the reaction will provide only very low levels of substrate cleavage.

The invention relates to an improved substrate and method, and uses thereof, for assaying RNase H activity. The substrate of the invention comprises an RNA/DNA heteroduplex molecule having a fluorophore and a quencher molecule. In the uncleaved substrate, the fluorescence emission of the fluorophore is quenched by the quencher molecule due to fluorescence resonance energy transfer (FRET; see below). Prior to applicants' work disclosed herein, a FRET-based RNase H assay and substrate therefor have not been described.

Fluorescence resonance energy transfer (FRET). Fluorescence resonance energy transfer is defined as the transfer of electronic excitation energy as a result of dipole-dipole interactions between the energy donor and the energy acceptor. The efficiency of energy transfer (and hence the extent of fluorescence quenching) is defined by Forster's equation:

$$E=R_0^6/(R_0^6+r^6)$$

where E is the efficiency of energy transfer, $R_0$ is the Forster distance at which the energy transfer rate is equal to the decay rate of the donor in the absence of acceptor, and r is the distance between donor and acceptor. It is apparent from this equation that the distance between donor and acceptor is an important factor in the efficiency of energy transfer and thus in the extent of donor emission quenching noted in the system. The closer the donor and acceptor, the more extensive the quenching, and thus the lower the background fluorescence signal. This translates into an improved signal-to-noise factor, which impacts on the overall sensitivity of the assay system.

The present invention relates to methods and reagents for the assay of ribonuclease H(RNase H) activity. In certain embodiments, a RNase H activity of a RNase H enzyme or of a multifunctional enzyme possessing RNase H activity may be assayed. In certain embodiments, such RNase H activity includes, but is not limited to RNase H activity associated with the reverse transcriptases of human pathogenic viruses such as the retroviruses HIV-1 and HIV-2, and the hepadnavirus hepatitis B virus. In further embodiments, such RNase H activity includes, but is not limited to RNase H activity associated with an RNase H enzyme of prokaryotic or eukaryotic origin, in an embodiment, of mammalian origin, in an embodiment, of human origin. In further embodiments, such RNase H activity includes, but is not limited to RNase H activity associated with RNase H1 and RNase H2 of eukaryotic or prokaryotic origin. The invention further relates to this method for the identification of compounds that may inhibit RNase H activity, including that associated with the reverse transcriptases of the human retroviruses HIV-1 and HIV-2 and the human hepadnavirus hepatitis B virus.

RNase H is unique among nucleases in that it selectively degrades the RNA component of an RNA/DNA hybrid duplex molecule, a double-strand nucleic acid comprised of one strand of RNA bound to a complementary strand of DNA.

The assay of the present invention uses an RNA/DNA duplex substrate, in an embodiment comprising a DNA oligonucleotide of, in embodiments, 14 to 24 nucleotides in length, modified with a quencher molecule. In embodiments, the oligonucleotide may be 15, 16, 17, 18, 19, 20, 21, 22 or 23 nucleotides in length. Also contemplated are numerical ranges defined by combinations of these values. The quencher molecule may be attached at either the 3'-end or the 5'-end or internally. The DNA oligonucleotide is annealed to a complementary, in an embodiment, a substantially complementary, in a further embodiment, an exactly complementary, RNA oligonucleotide of, in certain embodiments, 14 to 24 nucleotides in length, modified with a fluorophore. Similarly, the fluorophore may be attached at the 5'-end or the 3'-end or internally. The quencher and fluorophore are located within the heteroduplex such that they are in sufficiently close proximity for fluorescence resonance transfer to occur and as a result for the quencher molecule to be capable of exerting a quenching effect on the fluorophore. In an embodiment, the quencher may be at an end of the DNA oligonucleotide and the fluorophore at an end of the RNA oligonucleotide, with these two groups being juxtaposed at the same end of the heteroduplex molecule, i.e. the fluorophore is attached to the end of the RNA oligonucleotide which is complementary to that end of the DNA oligonucleotide that is modified with the quencher of fluorescence (i.e. fluorophore-5'DNA with quencher-3'RNA or vice versa). In an embodiment, the quencher of fluorescence is a non-fluorescent quencher of fluorescence. When the quencher-DNA/fluorophore-RNA duplex is formed, the fluorescence emission of the fluorophore is quenched, i.e. reduced as compared to a duplex lacking a quencher molecule. Degradation of the fluorophore-RNA strand by RNase H produces small fragments of RNA including that containing the fluorophore-modified ribonucleotide, which dissociates from the intact complementary DNA strand. This dissociation removes the quencher-mediated quenching and provides a fluorescent signal. The rate of increase in this signal is directly proportional to the extent of RNase H mediated cleavage of the RNA strand of the RNA/DNA duplex, and is readily measured in standard fluorometers. In addition, the assay is easily adapted to an array format, for example, a 96-well or 384-well microplate format, measurable in commercial microplate spectrofluorometers, and therefore suitable for high-throughput screening assays directed at the identification of modulators, in embodiments, inhibitors, of RNase H activity.

In a similar manner, the above noted components may be reversed to use a quencher-RNA molecule with a fluorophore-DNA molecule to form a quencher-RNA/fluorophore-DNA duplex, which may subsequently undergo RNaseH cleavage to yield an increase in fluorescence signal. Further, each of the DNA or RNA oligo nucleotide may have more than one quencher or fluorophore molecule attached thereto (see for example SEQ ID NOs 5 and 6), as long as a fluorophore has a quencher molecule in sufficiently close proximity to have a quenching effect in the uncleaved substrate, and such quenching is reduced to generate a sufficient increase in fluorescence emission signal upon cleavage of the substrate. As such, various arrangements/configurations of fluorophore and quencher molecule on the substrate may be utilized without departing from the invention. For example, in embodiments where the fluorophore and quencher molecules are attached to an end of the oligonucleotides, the possible configurations which may be used include, but are not limited to, the following (F=fluorophore; Q=quencher):

5' F-DNA oligonucleotide 3'
3' Q-RNA oligonucleotide 5'
5' Q-DNA oligonucleotide 3'
3' F-RNA oligonucleotide 5'
5' DNA oligonucleotide-F 3'
3' RNA oligonucleotide-Q 5'
5' DNA oligonucleotide-Q 3'
3' RNA oligonucleotide-F 5'
5' F-DNA oligonucleotide-F 3'
3' Q-RNA oligonucleotide-Q 5'
5' Q-DNA oligonucleotide-Q 3'
3' F-RNA oligonucleotide-F 5'
etc.

A "fluorophore" is any molecule capable of emitting light when illuminated/excited by light of an appropriate wavelength. A "quencher" is any molecule capable of accepting (or absorbing) the electronic energy emitted by a "fluorophore" when this "fluorophore" is illuminated/excited by light of an appropriate wavelength. The "quencher" provides a "quenching" effect on the fluorophore, thus reducing the fluorescence emission of the fluorophore in the uncleaved substrate. A number of fluorophores and quenchers are known in the art (see for example Richard P. Haugland, *Handbook of Fluorescent Probes and Research Products*, eighth edition, published by Molecular Probes, Eugene, Oreg., USA).

Accordingly, the invention provides a substrate suitable for assaying ribonuclease H activity; the substrate comprising:

(e) an RNA oligonucleotide;
(f) a DNA oligonucleotide hybridized to the RNA oligonucleotide to form a heteroduplex molecule;
(g) a fluorophore attached to one of the RNA or DNA oligonucleotides; and
(h) a quencher molecule attached to the other of the RNA or DNA oligonucleotides;

wherein the fluorophore and the quencher molecule are located within close proximity of each other in the heteroduplex molecule such that fluorescence emission of the fluorophore in the heteroduplex molecule is reduced as compared to a corresponding fluorescence emission in a corresponding heteroduplex molecule lacking the quencher molecule.

Substantially complementary nucleic acids are nucleic acids in which the "complement" of one molecule is substantially identical to the other molecule. Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48:443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information (through the internet at http://www.ncbi.nlm.nih.gov/). The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO$_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M NaHPO$_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

"Hybridized to" as used above refers to the association between the RNA and DNA oligonucleotides via standard Watson-Crick base pairing. As such, the DNA and RNA oligonucleotide sequences have between them a degree of complementarity to provide a sufficiently stable heteroduplex structure in the assay conditions used. In an embodiment, the DNA and RNA oligonucleotides are exactly complementary, meaning that across the entire length of the shorter of the two, the bases are matched exactly (G with C, T with A, U with A).

The sequence of the RNA oligonucleotide is such that the RNA/DNA duplex substrate is stable at temperatures normally used to carry out enzyme reactions in vitro (e.g., from 15 to 40° C., in an embodiment, 35 to 39° C., in an embodiment, 36 to 38° C. in an embodiment, 37° C.), and that the initial cut or cuts by ribonuclease H is/are such to produce a fluorophore-labeled RNA fragment of a sufficiently small size (in an embodiment, less than or equal to 6 ribonucleotides) that it rapidly dissociates from the quencher-labeled DNA oligonucleotide, thereby providing an increase in fluorescence emission that is directly proportional to the rate of cleavage of the RNA.

The stability of the RNA/DNA duplex may be controlled by various factors such as oligonucleotide length, oligonucleotide sequence and reaction conditions, most notably temperature, as well as for example the presence of salt and other compounds (e.g. detergents). Controlling stability via the oligonucleotide sequence refers to differences in stability inherent to different base pairs. For example, GC base pairs are more stable than AT base pairs, due to differences in the degree of hydrogen bonding. Therefore, all these parameters may be altered depending on the specific assay requirements desired under any set of conditions. The goal of manipulating such reaction conditions shall in general be toward optimizing the signal to noise ratio for the reaction, i.e. to result in an optimal change in fluorescence between the uncleaved and the cleaved states of the substrate.

In embodiments, the fluorophore/quencher pair is chosen such that the maximal increase in fluorescence emission of the fluorophore upon ribonuclease H cleavage of the RNA is at least 8-fold greater than the background fluorescence. In further embodiments, the maximal increase in fluorescence emission is 10, 12, 14, 15, 16, 18, 20, 22, 24 or 25-fold greater than the background fluorescence.

In an embodiment, the fluorophore may be fluorescein. Fluorescein is a commonly used fluorescent agent of high quantum efficiency (excitation/emission maxima of 494/520 nm). In an embodiment, the quencher is a non-fluorescent quencher. In an embodiment, a suitable non-fluorescent quencher of fluorescence may be a compound such as 4-((4-(dimethylamino)phenyl)azo)benzoic acid (DABCYL). In the absence of the quencher-DNA strand, illumination of the fluorescein-RNA with light at 495 nm will produce a strong light emission at 520 nm, due to the fluorescence of fluorescein. When the fluorescein-RNA/DABCYL-DNA duplex is formed, the fluorescence emission of fluorescein is strongly quenched, due to the fluorescence resonance energy transfer (FRET) of the energy emitted by the donor fluorescein to the acceptor DABCYL. Thus, illumination of the fluorescein-RNA/DABCYL-DNA duplex with light at 495 nm will no longer produce a strong light emission at 520 nm, due to the absorption of the fluorescein light emission energy by the quencher DABCYL. Treatment of the fluorescein-RNA/DABCYL-DNA duplex substrate with ribonuclease H results in enzymatic hydrolysis of the phosphodiester linkages of the fluorescein-RNA strand, producing small fragments of RNA including that containing the fluorescein-modified ribonucleotide. These small fragments of RNA readily dissociate from the intact complementary DNA strand. This dissociation removes the DABCYL-mediated quenching of the fluorescein thereby providing a fluorescent signal when the mixture is illuminated with light at 495 nm. The rate of increase in this signal is directly proportional to the extent of RNase H mediated cleavage of the RNA strand of the RNA/DNA duplex, and is readily measured in standard fluorometers.

Accordingly, the invention provides a method for assaying ribonuclease H activity in a sample, said method comprising:
  (a) measuring a first level of fluorescence emission of the fluorophore of the above-mentioned substrate in the absence of said sample;
  (b) contacting the substrate with said sample; and
  (c) measuring a second level of fluorescence emission in the presence of said sample;

wherein an increase in said second level relative to said first level is indicative of ribonuclease H activity.

The assay/method of the invention is easily adapted to a multi-well/sample format, such as a 96-well or 384 well microplate format, measurable in commercial microplate spectrofluorometers, and therefore suitable for use in high-throughput screening assays directed at the identification of compounds capable of modulating, in an embodiment, inhibiting, RNase H activity. "Modulating(ion)" as used herein, in various embodiments, encompasses both inhibiting/reducing activity and activating/increasing activity.

Accordingly, the invention provides a method of identifying a compound capable of modulating ribonuclease H activity, said method comprising:
  (a) contacting a source of enzymatically active ribonuclease H with a test compound and the substrate described above to form a reaction mixture;
  (b) measuring a first level of fluorescence emission of said fluorophore;
  (c) comparing said first level of fluorescence emission with a second level of fluorescence emission obtained from a corresponding control reaction mixture lacking said test compound;
  (d) selecting said test compound if said first level of fluorescence emission is different from said second level of fluorescence emission.

In an embodiment, the first level of fluorescence emission is less than the second level of fluorescence emission and the test compound is capable of inhibiting ribonuclease H activity.

The invention further provides a method of identifying or characterizing a compound capable of modulating ribonuclease H activity, said method comprising:
(a) contacting a source of enzymatically active ribonuclease H with a test compound and the above-mentioned substrate of to form a reaction mixture;
(b) measuring a test level of fluorescence emission of said fluorophore; and
(c) comparing said test level of fluorescence emission with a control level of fluorescence emission obtained from a corresponding control reaction mixture lacking said test compound;

wherein a difference between said test level and said control level is indicative that said test compound is capable of modulating ribonuclease H activity. In an embodiment the test level is less than the control level and the compound is capable of inhibiting RNase H activity.

In an embodiment, the assay method may be used to identify a compound which selectively modulates, in an embodiment, selectively inhibits, the activity associated with a particular source of RNase H activity. For example, such a compound may modulate, in an embodiment inhibit, RNase H activity associated with a reverse transcriptase enzyme, for example from HIV-1, HIV-2 or a hepadnavirus such as human hepatitis B virus, without significantly modulating, in an embodiment inhibiting, the RNase H activity associated with a eukaryotic, in an embodiment mammalian, in an embodiment human, RNase H.

In embodiments the above assay may be applied to a single test compound or to a plurality or "library" of such compounds (e.g. a combinatorial library). In the latter case, synergistic effects provided by combinations of compounds may also be identified and characterized.

Such assay systems may comprise a variety of means to enable and optimize useful assay conditions. Such means may include, but are not limited to suitable buffer solutions, for example, for the control of pH and ionic strength and to provide any necessary components for RNase H activity and stability and temperature control means. The pH values may range between pH 4 to pH 10, preferably between pH 6 to pH 9, and most preferably between pH 7 and pH 8.5. The ionic strength of the assay medium may be controlled by the presence of suitable salts such as NaCl or KCl in concentrations ranging between 0 and 1M, preferably between 1 mM and 250 mM, and most preferably between 20 mM and 100 mM. In embodiments the assay also includes a suitable divalent metal cation, such as $Mg^{2+}$ or $Mn^{2+}$, in concentrations ranging between 0 and 0.5 M, preferably between 1 mM and 50 mM, and most preferably between 2.5 mM and 10 mM. The divalent metal cation may be for example added in the form of $MgCl_2$, $MgSO_4$, $MnCl_2$, $MnSO_4$, or other suitable salt. Examples of suitable assay conditions for the measurement of RNase H activity are described in Rychetsky et al, Development of a nonradioactive ribonuclease H assay, Analytical Biochemistry 239: 113-115, 1996; Borkow et al, Inhibition of the ribonuclease H and DNA polymerase activities of HIV-1 reverse transcriptase by N-(4-tert-butylbenzoyl)-2-hydroxy-1-naphthaldehyde hydrazone, Biochemistry 36:3179-3185, 1997; Wisniewski et al, The sequential mechanism of HIV reverse transcriptase RNase H, Journal of Biological Chemistry 275:37664-37671, 2000; Snyder & Roth, Assays for retroviral RNase H, Methods in Enzymology 341:440-452, 2001.

The assay may be carried out in vitro utilizing a source of RNase H which may comprise naturally isolated or recombinantly produced RNase H, in preparations ranging from crude to pure. Recombinant RNase H and/or HIV-1 reverse transcriptase (with associated RNase H) may be produced in a number of prokaryotic or eukaryotic expression systems which are well known in the art. Some examples of the preparation of ribonucleases H suitable for use in the assay are found in the following references: for bacterial RNase H, Kanaya S, Prokaryotic type 2 RNases H, Methods in Enzymology 341:377-394, 2001; for yeast RNase H, Crouch R J et al, RNase H1 of Saccharomyces cerevisiae: methods and nomenclature, Methods in Enzymology 341:395-413, 2001; for human RNase H, Lima W F et al, Human RNases H, Methods in Enzymology 341:430-440, 2001; for HIV-1 RNase H, Smith J S and Roth M J, Purification and characterization of an active human immunodeficiency virus type 1 RNase H domain, Journal of Virology 67:4037-4049, 1993; for HIV-1 reverse transcriptase associated RNase H, Fletcher R S et al, Single step purification of HIV-1 recombinant wild type and mutant reverse transcriptase, Protein Expression and Purification 7:27-32, 1996. Such assays may be performed in an array format. In certain embodiments, one or a plurality of the assay steps are automated. Such assays may be performed in a cell-based or cell-free system.

A homologue, variant and/or fragment of RNase H which retains activity may also be used in the methods of the invention. Homologues include protein sequences which are homologous to, i.e. substantially identical to the amino acid sequence of an RNase H, sharing significant structural and functional homology with an RNase H. Variants include, but are not limited to, proteins or peptides which differ from an RNase H by any modifications, and/or amino acid substitutions, deletions or additions. Such variants include for example recombinantly-produced fusion proteins bearing for example tags facilitating purification and/or detection (e.g. multiple H is residues [e.g. six-His tag], glutathione-S-transferase [GST] fusions, influenza hemaglutinin antigen [HA]-tag, FLAG-tag, c-myc tag, etc.). Modifications can occur anywhere including the polypeptide backbone, (i.e. the amino acid sequence), the amino acid side chains and the amino or carboxyl termini. Such substitutions, deletions or additions may involve one or more amino acids. Fragments include a fragment or a portion of an RNase H or a fragment or a portion of a homologue or variant of an RNase H.

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a sequence is "homologous" to another sequence if the two sequences are substantially identical and the functional activity of the sequences is conserved (as used herein, the term 'homologous' does not infer evolutionary relatedness). For example, two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. As used herein, a given percentage of homology between sequences denotes the degree of sequence identity in optimally aligned sequences. An "unrelated" or "non-homologous" sequence shares less than 40% identity, though preferably less than about 25% identity, with a subject sequence.

The invention further relates to commercial packages or kits for carrying out the assay and screening methods noted above, comprising the appropriate above-mentioned reagents together with instructions for a method of assaying RNase H activity and/or identifying a compound capable of modulating, in an embodiment inhibiting, RNase H activity.

Therefore, the invention further provides a commercial package comprising the above-mentioned substrate together with instructions for assaying RNase H activity in a sample.

The invention further provides a commercial package comprising the above-mentioned substrate together with instructions for identifying a compound capable of modulating, in an embodiment inhibiting, RNase H activity.

The invention further provides a use of the above-mentioned substrate for assaying RNase H activity in a sample; as well as for identifying a compound capable of modulating, in an embodiment inhibiting, RNase H activity.

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the claims, the word "comprising" is used as an open-ended term, substantially equivalent to the phrase "including, but not limited to". The following examples are illustrative of various aspects of the invention, and do not limit the broad aspects of the invention as disclosed herein.

EXAMPLES

Example 1

Preparation of the Fluorophore-RNA/Quencher-DNA Hybrid Duplex Substrate

An example of a suitable substrate for use in the assay of the present invention comprises an RNA oligonucleotide modified at the 3'-end with Aminolink-2 and derivatized with fluorescein isothiocyanate, to provide a modified RNA oligonucleotide of the sequence 5'-GAU CUG AGC CUG GGA GCU-fluorescein-3' (SEQ ID NO: 1), annealed to a complementary DNA oligonucleotide modified at the 5'-end with Aminolink-2 and derivatized with the FRET acceptor DABCYL succinimidyl ester, to provide a modified DNA oligonucleotide of the sequence 5'-DABCYL-AGC TCC CAG GCT CAG ATC-3' (SEQ ID NO: 2).

Alternatively, the substrate for use in the present invention is an RNA oligonucleotide modified at the 5'-end with Aminolink-2 and derivatized with fluorescein isothiocyanate, to provide a modified RNA oligonucleotide of the sequence 5'-fluorescein-GAU CUG AGC CUG GGA GCU-3' (SEQ ID NO: 3), annealed to a complementary DNA oligonucleotide modified at the 3'-end with Aminolink-2 and derivatized with the FRET acceptor DABCYL succinimidyl ester, to provide a modified DNA oligonucleotide of the sequence 5'-AGC TCC CAG GCT CAG ATC-DABCYL-3' (SEQ ID NO: 4).

Alternatively, the substrate for use in the present invention is an RNA oligonucleotide modified at both the 3'-end and the 5'-end with Aminolink-2 and derivatized with fluorescein isothiocyanate, to provide a modified RNA oligonucleotide of the sequence 5'-fluorescein-GAU CUG AGC CUG GGA GCU-fluorescein-3' (SEQ ID NO: 5), annealed to a complementary DNA oligonucleotide modified at both the 5'-end and the 3'-end with Aminolink-2 and derivatized with the FRET acceptor DABCYL succinimidyl ester, to provide a modified DNA oligonucleotide of the sequence 5'-DABCYL-AGC TCC CAG GCT CAG ATC-DABCYL-3' (SEQ ID NO: 6).

Figure 1:
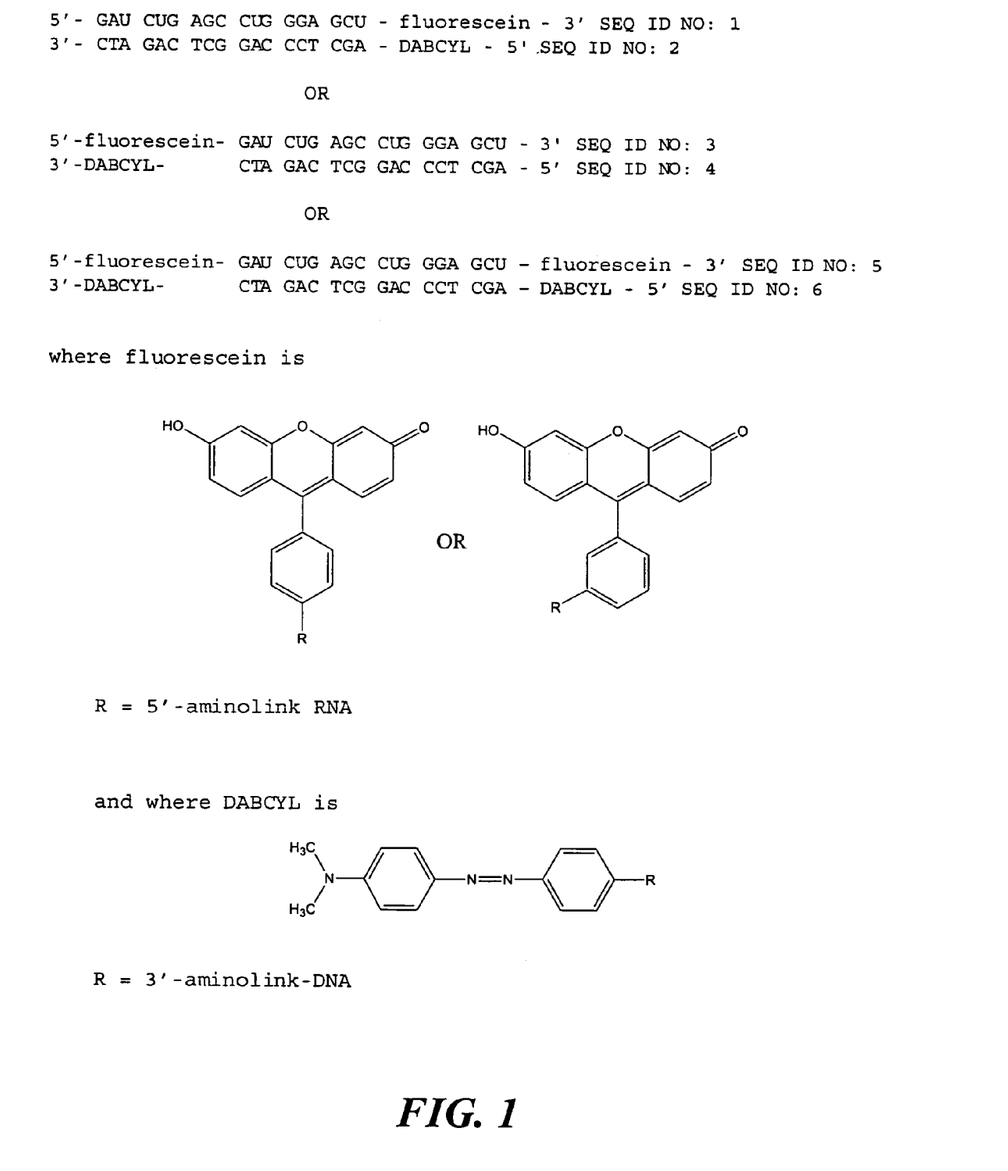
FIG. 1. Structure of RNA/DNA hybrid duplex substrates for use in the FRET assay of ribonuclease H activity according to certain embodiments of the invention.

Structures of the RNA/DNA duplex substrate molecules described in this example are shown in FIG. 1. The fluorescent- and quencher-labelled oligonucleotides used in the studies described herein were ordered to specification and purchased from Trilink Biotechnologies.

Figure 2:
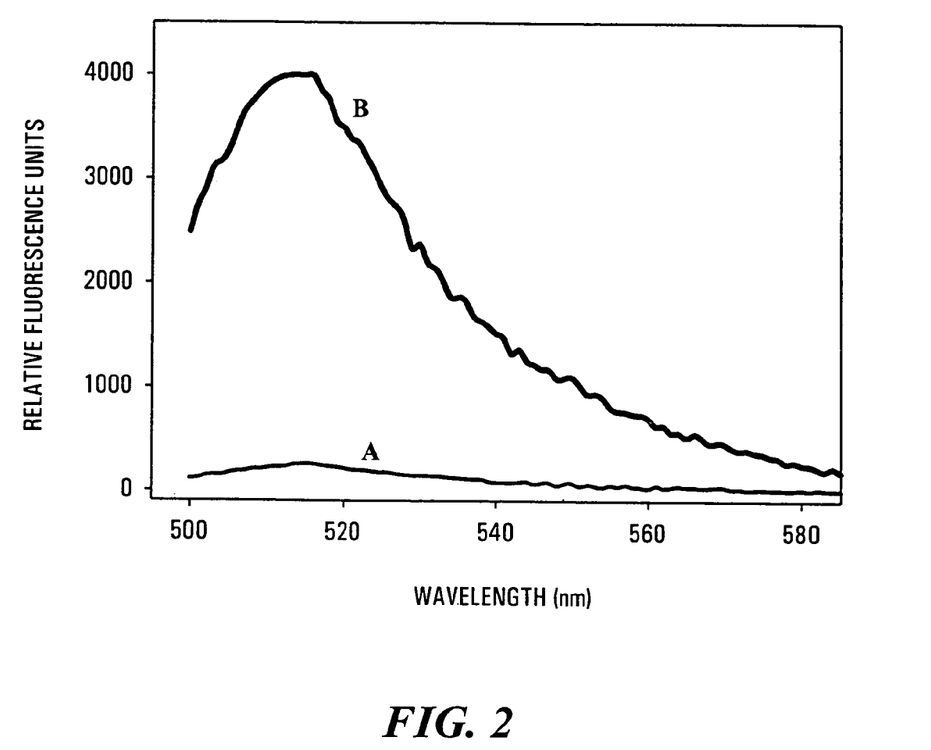

To prepare the 3'-fluorescein-RNA/5'-DABCYL-DNA hybrid duplex substrate, a known amount of 3'-fluorescein-RNA was dissolved in 20 mM Tris buffer (pH 8.0, 37° C.) to provide a final concentration of 5 µM. Two equivalents of the 5'-DABCYL-DNA oligonucleotide were added, and the mixture was heated to 90° C. for 5 min and cooled slowly to room temperature. The structure of the resulting RNA/DNA hybrid duplex substrate is provided in FIG. 1. The positioning of the fluorescein donor at the 3'-end of the RNA oligonucleotide and the DABCYL acceptor at the 5'-end of the DNA oligonucleotide provides a very close proximity of the donor and acceptor, unlike the situation in other nuclease FRET assays[14-16]. This results in a very intense quenching of the fluorescein emission in the intact RNA/DNA hybrid duplex substrate due to the spectral overlap of the fluorescence emission of fluorescein with the absorption spectrum of DABCYL. In addition, DABCYL is non-fluorescent, and thus cannot contribute any light emission. Both of these factors result in a very low background and provide a high signal-to-noise in the assay measurements, as shown in FIG. 2. The ratio of the donor fluorescence in the absence and in the presence of its quencher is approximately fifteen-fold.

Similarly, the positioning of the fluorescein donor at the 5'-end of the RNA oligonucleotide and the DABCYL acceptor at the 3'-end of the DNA oligonucleotide also provides a very close proximity of the donor and acceptor, which also leads to a strong quenching of the fluorescein emission.

Microplate assay protocol for the measurement of RNase H activity using the RNA/DNA hybrid duplex substrate. Reaction assay mixtures contained 5 µl of a stock solution of 2.5 µM RNA/DNA hybrid duplex substrate added to 85 µl of assay buffer (50 mM Tris, pH 8.0, 37° C., containing 60 mM KCl and 2.5 mM $MgCl_2$), prepared in the wells of a 96-well fluorescence microtiter plate, and warmed to 37° C. using the temperature control of the SpectraMax Gemini XS microplate spectrofluorometer (Molecular Devices). Reactions were started by the addition of 5 µl of a solution of recombinant HIV-1 reverse transcriptase (usually providing a final concentration of 2.5 nM of the p51/p66 RT heterodimer in the assay, and mixing using the automatic mixing function of the microplate spectrofluorometer. The reverse transcriptase for use in this assay was prepared as described by Fletcher R S et al, Single step purification of HIV-1 recombinant wild type and mutant reverse transcriptase, Protein Expression and Purification 7:27-32, 1996. The increase in fluorescence signal resulting from the loss of FRET due to the enzymatic hydrolysis of the RNA strand was measured over suitable time intervals (ranging from 3 minutes to 60 minutes), at an excitation wavelength of 490 nm and an emission wavelength of 528 nm, using a cut-off filter of 515 nm. Data analysis and curve fitting were carried out using the appropriate transform functions of the software SigmaPlot 2000 (SPSS Inc.).

Example 2

Fluorescence Emission Spectra of the 3'-Fluorescein-RNA/5'-DABCYL-DNA Hybrid Duplex Substrate Before and After Treatment with HIV-1 RT RNase H A volume of 3'-fluorescein-RNA/5'-DABCYL-DNA hybrid duplex substrate solution containing 60 µmol of the oligonucleotide duplex was added to 300 µl reaction buffer comprising 50 mM Tris/HCl (pH 8.0, 37° C.) and containing 60 mM KCl and 2.5 mM $MgCl_2$, in a spectrofluorometer cuvette. The solution was excited with light at 490 nm, and the steady-state fluorescence spectrum was recorded using a Quanta Master QM-1 T-format fluorescence spectrometer (Photon Technology International, Princeton, N.J.). Virtually no fluorescence emission was noted over the range of 500 to 600 nm, proving that the 3'-fluorescein-RNA/5'-DABCYL-DNA hybrid duplex substrate was a very efficient FRET system. Following recording of the unreacted FRET spectrum, an aliquot of HIV-1 RT was added to provide a final concentration of 2.5 nM of p51/p66 RT. The sample was mixed, and allowed to incubate at 37° C. for 30 minutes. The solution was again excited with light at 490 nm, and the steady-state fluorescence spectrum was recorded over the range of 500 to 600 nm. A large increase in fluorescence emission was seen, with a peak between 515-530 nm. The fluorescence emission at 518 nm of the RT-reacted substrate was approximately 15-fold greater than that of the unreacted substrate. The results of these experiments are shown in FIG. 2.

Example 3

Effect of RNase H Concentration on the Time Dependence of the FRET Assay

Figure 3A:
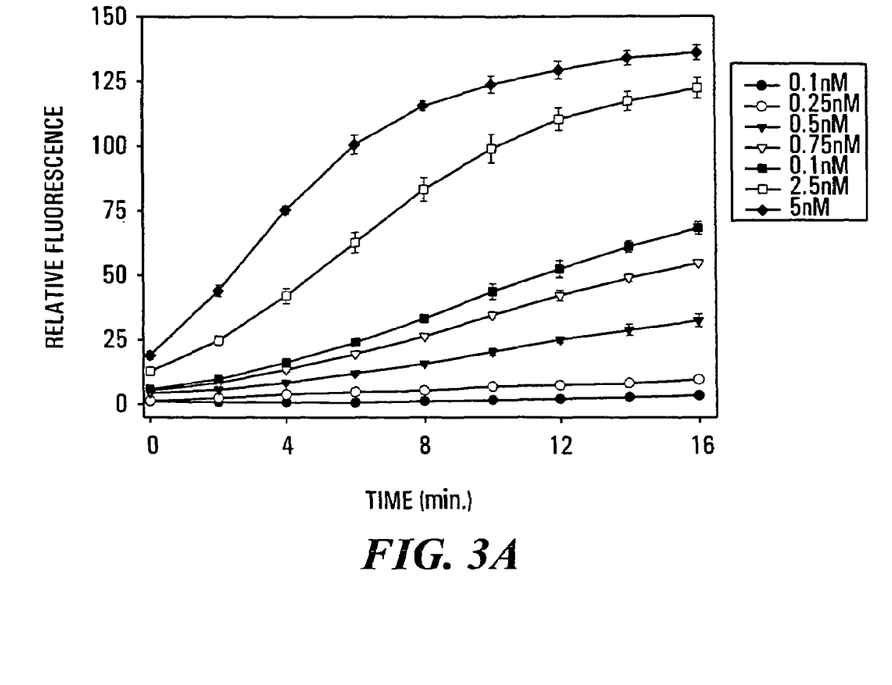
Figure 3B:
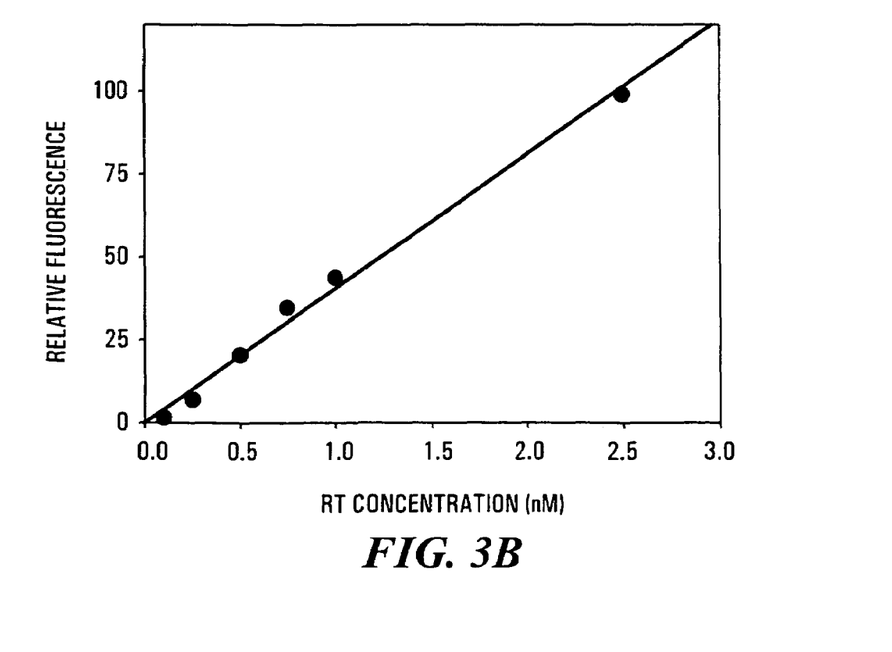

Aliquots of 85 µl of 50 mM Tris/HCl (pH 8.0, 37° C.), containing 60 mM KCl and 2.5 mM $MgCl_2$, and 0.2 µM of 3'-fluorescein-RNA/5'-DABCYL-DNA hybrid duplex substrate were added to individual wells of a fluorescence microtiter plate and warmed to 37° C. using the temperature control of the SpectraMax Gemini XS microplate spectrofluorometer. Reactions were started by the addition of 5 µl of various solutions of recombinant HIV-1 reverse transcriptase (RT) such that the final concentration of RT in the individual assays ranged from 0.1 nM to 5 nM of p51/p66 heterodimer, and mixing using the automatic mixing function of the microplate spectrofluorometer. The increase in fluorescence at 528 nm was measured at regular time intervals using excitation at 490 nm and a 515 nm cut-off filter. Under these conditions, the rate of increase of fluorescence emission at 528 nm was found to be directly proportional to the concentration of RT in the assay. The results of these experiments are shown in FIG. 3.

Example 4

Determination of the Affinity Constant for the Interaction of the 3'-Fluorescein-RNA/5'-DABCYL-DNA Hybrid Duplex Substrate with HIV-1 Reverse Transcriptase Aliquots of 85 µl of 50 mM Tris/HCl (pH 8.0, 37° C.), containing 60 mM KCl and 2.5 mM $MgCl_2$, and variable amounts of 3'-fluorescein-RNA/5'-DABCYL-DNA hybrid duplex substrate (ranging from 10 to 200 nM final concentration) were added to individual wells of a fluorescence microtiter plate and warmed to 37° C. using the temperature control of the SpectraMax Gemini XS microplate spectrofluorometer. Reactions were started by the addition of 5 µl of a solution of recombinant HIV-1 reverse transcriptase such that the final concentration of RT in the individual assays was 1.5 nM of p51/p66 heterodimer, with mixing using the automatic mixing function of the microplate spectrofluorometer. The increase in fluorescence at 528 nm was measured at regular time intervals using excitation at 490 nm and a 515 nm cut-off filter. Under these conditions, the initial rate of increase of fluorescence emission at 528 nm was found to be proportional to the concentration of the 3'-fluorescein-RNA/5'-DABCYL-DNA hybrid duplex substrate in the assay. The variation in initial rate of fluorescence emission with 3'-fluorescein-RNA/5'-DABCYL-DNA hybrid duplex substrate concentration followed hyperbolic or saturation kinetics. The results of these experiments were analyzed by Lineweaver-Burk plot methods, providing a $K_m$ value of 40 nM for the interaction of RT with the 3'-fluorescein-RNA/5'-DABCYL-DNA hybrid duplex substrate.

Example 5

Comparison of the FRET Rnase H Assay with the Gel-Based RNase H Assay for the Identification of Inhibitors of HIV-1 RT RNase H In order to validate the FRET assay for use in the identification of RNase H inhibitors, the inhibition curves for the known inhibitor, N-(4-tert-butylbenzoyl)-2-hydroxy-1-naphthaldehyde hydrazone (BBNH)[17], obtained with the FRET assay, was compared with similar data obtained using the standard gel electrophoretic assay.

Aliquots of 85 µl of 50 mM Tris/HCl (pH 8.0, 37° C.), containing 60 mM KCl and 2.5 mM $MgCl_2$, 1.5 nM p51/p66 RT and variable amounts of BBNH were added to individual wells of a fluorescence microtiter plate and incubated at 37° C. for 15 minutes using the temperature control of the SpectraMax Gemini XS microplate spectrofluorometer. Reactions were started by the addition of 5 µl of a solution of 3'-fluorescein-RNA/5'-DABCYL-DNA hybrid duplex substrate (final concentration of 100 nM in the assay), with mixing using the automatic mixing function of the microplate spectrofluorometer. The increase in fluorescence at 528 nm was measured at regular time intervals using excitation at 490 nm and a 515 nm cut-off filter. Ten different concentrations of BBNH (ranging from 0 to 20 µM final assay concentration), each assayed in triplicate, were assayed simultaneously in a single microtiter plate, in a total time of 15 minutes. The resulting inhibition data were analyzed using the transform functions of Sigmaplot 2000.

The gel electrophoretic assay used 5'-[$^{32}$P]-RNA of the sequence 5'-GAU CUG AGC CUG GGA GCU-3' (SEQ ID NO: 7; identical to that of the FRET RNA, but lacking the 3'-fluorescein), prepared by the transfer of $^{32}$P from [γ-$^{32}$P]-ATP in a reaction catalyzed by bacteriophage T4 polynucleotide kinase. This 5'[$^{32}$P]-RNA oligonucleotide was annealed to complementary unlabeled DNA of the sequence 5'-AGC TCC AGG CTC CAG ATC-3' (SEQ ID NO: 8) to form the [$^{32}$P]-RNA/DNA hybrid duplex substrate. Aliquots of 100 µl of 50 mM Tris/HCl (pH 8.0, 37° C.), containing 60 mM KCl and 2.5 mM $MgCl_2$, 1.5 nM p51/p66 RT and variable amounts of BBNH inhibitor were added to individual microtubes and incubated at 37° C. for 15 minutes. Reactions were initiated by the addition of [$^{32}$P]-RNA/DNA hybrid duplex substrate (final concentration 100 nM), and assay tubes were incubated at 37° C. Aliquots were removed at different times, and the reactions were stopped by the addition of an equal volume of denaturing gel loading buffer (98% deionized formamide containing 10 mM EDTA, 1 mg/ml bromophenol blue and 1 mg/ml xylene cyanol). The reaction products were denatured by heating at 100° C. for 5 minutes, then loaded onto a 16% polyacrylamide sequencing gel containing 7 M urea and the products resolved by electrophoresis. The resolved reaction products were then visualized by autoradiography. The extent of RNase H activity can be determined quantitatively by densitometric analysis of the time-dependent disappearance of the full-length RNA substrate and/or the appearance of the smaller degradation products. In this experiment, the bands corresponding to the undegraded 18 nucleotide 5'-[$^{32}$P]-RNA were quantified by densitometry, using the software UN-SCAN-IT (Silk Scientific, Orem, Utah). The IC$_{50}$ values for BBNH inhibition of HIV-1 RT associated RNase H activity were calculated from plots of the residual undegraded 5'[$^{32}$P]-RNA vs. drug concentration.

The results of the experiment comparing the FRET RNase H assay and the gel electrophoresis RNase H assay for the determination of inhibitor potency are presented in Table 1.

TABLE 1

Comparison of IC$_{50}$ values for inhibition of HIV-1 RT associated RNase H by N-(4-tert-butylbenzoyl)-2-hydroxy-1-naphthaldehyde hydrazone (BBNH) obtained using the FRET assay and the gel electrophoretic assay.

| IC$_{50}$ for BBNH obtained with the FRET assay | IC$_{50}$ for BBNH obtained with the gel assay |
|---|---|
| 2.6 ± 0.5 | 3.0 ± 1.2 |

All references cited are herein incorporated by reference.

REFERENCES

1. R. J. Crouch and J. J. Toulme, eds. (1998) "Ribonucleases H". Les Editions INSERM, Paris).
2. M. A. Parniak and N. Sluis-Crèmer (2000) Adv. Pharmacol. 49, 67-109.
3. M. C. Starnes and Y. C. Cheng (1989) J. Biol. Chem. 264, 7073-7077.
4. A. D. Papahilis and E. F. Kamper (1985) Analyt. Biochem. 145, 160-169.
5. P. L. Carl, L. Bloom and R. J. Crouch (1980) J. Bacteriol. 144, 28-35.
6. P. Frank, C. Cazenave, S. Albert and J. J. Toulme (1994) Biochem. Biophys. Res. Commun. 196, 1552-1557.
7. L. Y. Han, W. P. Ma and R. J. Crouch (1997) Biotechniques 23, 920-926.
8. J. G. Starvianopoulos and E. Chargaff (1976) Proc. Natl. Acad. Sci. USA 73, 1556-1558.
9. V. Mizrahi (1989) Biochemistry 28, 9088-9094.
10. L. DeDionisio and S. M. Gryaznov (1995) J. Chromatogr. B: Biomed. Appl. 669, 125-131.
11. P. Rychetsky, Z. Hostomska, Z. Hostomsky and P. Strop (1996) Analyt. Biochem. 239, 113-115.
12. E. Jay, R. Bambara, R. Padmanabhan and R. Wu (1974) Nucleic Acids Res. 1, 331-338.
13. L. W. McLaughlin, F. Benseler, E. Grawser, N. Piel and S. Scholtissek (1987) Biochemistry 26, 7238-7245.
14. S. S. Ghosh, P. S. E is, K. Blumeyer, K. Fearon and D. P. Millar (1994) Nucleic Acids Res. 22, 3155-3159.
15. S. P. Lee, D. Porter, J. G. Chirikjian, J. R. Knitson and M. K. Han (1994) Analyt. Biochem. 220, 377-383.
16. S. P. Lee, M. L. Censullo, H. G. Kim, J. R. Knutson and M. K. Han (1995) Analyt. Biochem. 227, 295-301.
17. G. Borkow, R. S. Fletcher, J. Barnard, D. Arion, D. Motakis, G. I. Dmitrienko and M. A. Parniak (1997) Biochemistry 36, 3179-3185.
18. Richard P. Haugland, *Handbook of Fluorescent Probes and Research Products*, eighth edition, published by Molecular Probes, Eugene, Oreg., USA.
19. Wisniewski et al, The sequential mechanism of HIV reverse transcriptase RNase H, Journal of Biological Chemistry 275:37664-37671, 2000.
20. Snyder & Roth, Assays for retroviral RNase H, Methods in Enzymology 341:440-452, 2001.
21. Kanaya S, Prokaryotic type 2 RNases H, Methods in Enzymology 341:377-394, 2001.
22. Crouch R J et al, RNase H1 of *Saccharomyces cerevisiae*: methods and nomenclature, Methods in Enzymology 341: 395-413, 2001.
23. Lima W F et al, Human RNases H, Methods in Enzymology 341:430-440, 2001.
24. Smith J S and Roth M J, Purification and characterization of an active human immunodeficiency virus type 1 RNase H domain, Journal of Virology 67:4037-4049, 1993.
25. Fletcher R S et al, Single step purification of HIV-1 recombinant wild type and mutant reverse transcriptase, Protein Expression and Purification 7:27-32, 1996.

What is claimed is:

1. A method of identifying or characterizing a compound that modulates ribonuclease H activity, said method comprising:
   (a) providing a substrate comprising:
      a heteroduplex molecule comprising a single-stranded RNA oligonucleotide and a single-stranded DNA oligonucleotide hybridized to said RNA oligonucleotide;
      a fluorophore attached to one of said RNA or DNA oligonucleotides; and
      a quencher molecule attached to the other of said RNA or DNA oligonucleotides;
      wherein said fluorophore and said quencher molecule are located within close proximity of each other in said heteroduplex molecule such that fluorescence emission of said fluorophore in said heteroduplex molecule is reduced as compared to a corresponding fluorescence emission in a corresponding heteroduplex molecule lacking said quencher molecule;
   (b) contacting a source of enzymatically active ribonuclease H with a test compound and said substrate to form a reaction mixture;
   (c) measuring a test level of fluorescence emission of said fluorophore; and
   (d) comparing said test level of fluorescence emission with a control level of fluorescence emission obtained from a corresponding control reaction mixture lacking said test compound;
   wherein a difference between said test level and said control level is indicative that said test compound modulates ribonuclease H activity.

2. The method according to claim 1, which method is a method of identifying or characterizing a compound that inhibits ribonuclease H activity and wherein, in step (c), if said test level of fluorescence emission is lower than said control level of fluorescence emission, said test compound is identified as an inhibitor of ribonuclease H activity.

3. The method according to claim 1, wherein said test compound is a plurality of test compounds and said reaction mixture is a plurality of respective reaction mixtures.

4. The method according to claim 3, wherein said plurality of reaction mixtures is selected from the group consisting of 2 to 96 reaction mixtures and 2 to 384 reaction mixtures.

5. The method according to claim 1, wherein said fluorophore is attached to an end of one of said RNA or DNA oligonucleotides.

6. The method according to claim 1, wherein said quencher molecule is attached to an end of the other of said RNA or DNA oligonucleotides.

7. The method according to claim 1, wherein said quencher molecule is attached to an end of one of said RNA or DNA oligonucleotides and said quencher molecule is attached to an end of the other of said RNA or DNA oligonucleotides, and wherein said fluorophore and said quencher molecule are juxtaposed at an end of said heteroduplex molecule.

8. The method according to claim 1, wherein said quencher molecule is non-fluorescent.

9. The method according to claim 1, wherein said RNA oligonucleotide, DNA oligonucleotide, or both, are 14-24 nucleotides in length.

10. The method according to claim 1, wherein said RNA oligonucleotide and said DNA oligonucleotide are exactly complementary.

11. The method according to claim 1, wherein said fluorophore is fluorescein.

12. The method according to claim 1, wherein said quencher molecule is DABCYL.

* * * * *